(12) United States Patent
Fuisz et al.

(10) Patent No.: US 6,277,406 B1
(45) Date of Patent: *Aug. 21, 2001

(54) EASILY PROCESSED TABLET COMPOSITIONS

(75) Inventors: Richard C. Fuisz, McLean; Tushar K. Misra, Leesburg; Pradeepkumar P. Sanghvi, Herndon, all of VA (US)

(73) Assignee: Fuisz Technologies Ltd., Chantilly, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/946,806

(22) Filed: Oct. 8, 1997

(51) Int. Cl.$^7$ ........................................... A61K 9/20
(52) U.S. Cl. ..................... 424/464; 424/465; 424/469; 424/472; 424/479
(58) Field of Search .................. 424/464, 465, 424/469, 472, 479

(56) References Cited

U.S. PATENT DOCUMENTS

| | | | |
|---|---|---|---|
| 5,429,836 | 7/1995 | Fuisz | 426/601 |
| 5,587,172 | 12/1996 | Cherukuri et al. | 424/401 |
| 5,616,344 | 4/1997 | Battist et al. | 424/486 |
| 5,622,719 | 4/1997 | Myers et al. | 424/488 |
| 5,637,326 | 6/1997 | Bogue et al. | 425/82.1 |
| 5,840,334 * | 11/1998 | Raiden et al. | 424/464 |
| 5,869,098 | 2/1999 | Misra et al. | 414/484 |

FOREIGN PATENT DOCUMENTS

| | | | |
|---|---|---|---|
| 687464 * | 12/1995 | (EP) . | |
| 9534293 * | 12/1995 | (WO) . | |
| WO 95/34290 | 12/1995 | (WO) | A61K/9/14 |
| WO 95/34293 | 12/1995 | (WO) | A61K/9/20 |

* cited by examiner

Primary Examiner—Thurman K. Page
Assistant Examiner—Lakshmi Channavajjala
(74) Attorney, Agent, or Firm—John F. Levis; Richard D. Schmidt

(57) ABSTRACT

The invention deals with the use of low temperature and low humidity conditions during the storage and shaping of "flash-dose" tablet compositions. The compositions may be rendered substantially non-amorphous before tablet formation.

6 Claims, No Drawings

EASILY PROCESSED TABLET COMPOSITIONS

BACKGROUND

The technology called "flash doses" produces dosage units which readily dissolve in the consumer's mouth. Tab-letting compositions using this concept have been described in U.S. Pat. Nos. 5,587,172, 5,616,344, and 5,622,719, all incorporated by reference and all assigned to Fuisz Technologies Ltd.

Dosage units, i.e., tablets, produced using "flash-dose" technology have better patient compliance than others because they dissolve so easily. However, "flash-dose" tablet mixes, prior to formation into tablets, are often difficult to handle. The mixes are partially amorphous with high cohesivity, so that they often are sticky and flow poorly in tableting devices. They tend to yield processing problems such as "bridging," "arching" and "ratholing."

Arching occurs when the mix forms a bridge across the mouth of a chute or other opening as material beneath the bridge continues onward. Ratholing is the propensity to flow from the middle leaving material clinging to the sides of the vessel or conduit.

There is a need for a method to modify the cohesive and adhesive nature of "flash-dose" tablet mixes and, thereby, reduce the stickiness which leads to arching, ratholing and other processing problems such as sticking and picking of tablets. This invention answers that need.

SUMMARY OF THE INVENTION

Applicants have discovered that decreasing the temperature of the partially amorphous shearform tablet mix, especially a mix containing glycerin, to a point below its glass transition temperature, while controlling the humidity to keep it low, minimizes sticking and improves the mix's flow properties. Also, the tableting procedure can be carried out at low humidity and low temperature to prevent sticking and picking problems, yielding tablets which dissolve quickly in the mouth.

Also, the invention provides a process by which the tablets' friability can be made from poorly flowing and cohesive shearform matrices which may be crystallized before tablet formation.

DETAILED DESCRIPTION OF THE INVENTION

The invention deals with processes for handling and tableting "flash-dose" tablet mixes and with dosage units made using those processes.

Unless otherwise stated, all parts stated are weight parts, based on the weight of the total composition.

The "flash-dose" tablet compositions are generally made from formulations containing a saccharide-based carrier, a bioaffecting agent and a binder. More than one of each of these can be used. In addition, the formulations also include one or more conventional excipients, i.e., fillers, lubricants, sweeteners, perfumes, effervescent agents, colorants, controlled release systems, coatings, crystallization modifiers and the like.

Typically, the ingredients, processes and devices disclosed in U.S. Pat. Nos. 5,587,172, 5,616,344, 5,622,719, and 5,637,326 are useful herein. The ingredients are those useful in making the shearform matrices, or flosses, described therein. These disclosures are hereby incorporated by reference.

The inventor deals with the use of at least one of the following techniques for improving the processability of tablet compositions:

i) storing the composition at low temperature and at controlled humidity; and ii) molding the composition at low temperature and at low humidity. Ideally, both techniques i) and ii) are used.

Improved processability is found when the cohesion of the tablet composition (i.e., that tendency of particles to stick or adhere to each other) is greater than its adhesion (i.e., the tendency for the composition's mass to stick to surfaces during storage, handling and/or molding).

By "low temperature" applicants mean a temperature below the glass transition temperature of the formulation. Ideally, that temperature will be below the melting point of any liquid binder, e.g., glycerin, which is used in the composition. Temperatures of less than 15° C. are used, with those between about −20° C. and 10° C. being highly effective.

"Controlled humidity" means that the tablet composition is stored in closed vessels, e.g., sealed containers, or is otherwise handled to ensure that its humidity does not exceed 40% relative humidity during storage. Relative humidity values of about 10% to about 30% are optimal.

When the temperature and humidity are kept low, the cohesion/adhesion ratio is maintained. Also, when the humidity is low, the condensation of moisture on the surface of the mix or on equipment is eliminated.

The feedstock for making shearform matrices includes a carrier which is capable of undergoing the physical and chemical changes associated with flash-flow processing. These carriers are carbohydrates, with saccharide-based materials being very effective.

Sugars, i.e., sucrose, fructose, lactose, and sugar alcohols, e.g., sorbitol, monitol, xylitol and the like, are useful feedstocks. Combinations of $C_5$ to $C_6$ sugars and sugar alcohols can be used, as well as mixtures containing mono-, di- and poly-saccharides and other suitable carriers.

During processing, the saccharide-based carriers are subjected to heat and optional shear forces sufficient to change their morphological properties and yield amorphous matrices.

The bioaffecting agents useful include a wide variety of substances. Among them are those in the following therapeutic categories: ace-inhibitors, analgesics, antacids, anti-anginal drugs, anti-arrhythmia agents, antiasthmatics, anticholesterolemics, anticonvulsants, antidepressants, antidiarrheal preparations, antihistamines, antihypertensives, anti-infectives, anti-inflammatories, anti-lipid agents, antimaniacs, antinauseants, antistroke agents, antithyroid preparations, anabolic drugs, antiparasitics, antipsychotics, antipyretics, antispasmodics, antithrombotics, anxiolytic agents, appetite stimulants, appetite suppressants, beta-blocking agents, bronchodilators, cardiovascular agents, cerebral dilators, chelating agents, cholecystekinin antagonists, chemotherapeutic agents, cognition activators, contraceptives, coronary dilators, cough suppressants, decongestants, deodorants, dermatological agents, diabetes agents, diuretics, emollients, enzymes, erthropoietic drugs, expectorants, fertility agents, fungicides, gastrointestinal agents, growth regulators, $H_2$-antagonists, hormone replacement agents, hyperglycemic agents, laxatives, migraine treatments, mineral supplements, mucolytics, narcotics, neuroleptics, neuromuscular drugs, non-steroidal anti-inflammatories (NSAIDs), nutritional additives, peripheral vasodilators, polypeptides, prostaglandins, psychotropics, renin inhibitors, respiratory stimulants, steroids, stimulants, sympatholytics, thyroid preparations, tranquilizers, uterine relaxants, vaginal preparations, vasoconstrictors, vertigo agents, vitamins, wound healing agents, and others.

Highly useful bioaffecting agents include analgesics, $H_2$-antagonists and antacids. Analgesics such as aspirin, acetaminophen and acetaminophen plus caffeine may be processed in accordance herewith.

$H_2$-antagonists contemplated include cimetidine, ranitidine, famotidine, rizatidine, ebratidine, mefintidine, roxatidine, pisotidine, aceroxatidine and their salts.

Antacids can be prepared from ingredients such as: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate of magnesium aluminum sulfate, magaldrate, magnesium aluminosilicate, magnesium carbonate, magnesium glycinate, magnesium hydroxide, magnesium oxide, magnesium trisilicate, milk solids, aluminum mono- or di-basic calcium phosphate, tricalcium phosphate, potassium bicarbonate, sodium tartrate, sodium bicarbonate, magnesium aluminosilicates, tartaric acids and salts, and the like. Mixtures are operable. Moreover, antacids can be used in combination with $H_2$-antagonists.

Other useful bioaffecting ingredients include antidiarrheals such as IMMODIUM AD, antihistamines, antitussives, decongestants, vitamins and breath fresheners. Also contemplated are anxiolytics such as XANAX, antipsychotics such as CLOZARIL and HALDOL, nonsteroidal antiinflammatories such as VOLTAREN and LODINE, antihistamines such as SELDANE, HISMANAL, RELAFEN and TAVIST, antiemetics such as KYTRIL and CESAMET, bronchodilators such as BENTOLIN, PROVENTIL, antidepressants such as PROZAC, ZOLOFT, and PAXIL, antimigraine agents such as IMIGRAN, ace-inhibitors such as VASOTEC, CAPOTEN and ZESTRIL, anti-Alzheimers agents such as NICERGOLINE, and $Ca^{II}$-antagonists such as PROCARDIA, ADALAT and CALAN.

The binders used herein include one or more optional substances which serve at least one of two functions: (1) to assist in the binding or cohesion of particulates in the tablet composition, and (2) to promote crystallization of the saccharide-based shearform matrices in the compositions. One useful binder is glycerin; another is lecithin, polyethylene glycol. One group of additives, termed "crystallization modifiers," can be used, before or after the shearform matrices have been made, to affect the crystalline character of the matrices.

Typically, about zero part to about 10 parts of one or more crystallization modifiers is used to promote crystallization after the matrices are formed. Useful crystallization modifiers include glycerin and various surfactants, e.g., lecithin, polyethylene glycol and polyoxyethylene sorbitan fatty acid esters, called "TWEENS."

Another group of additives, called "crystallization enhancers," include ethanol and other additives which, when brought into contact with the preformed matrices, cause them to crystallize. Use of about zero part to about 10 parts of one or more crystallization enhancers is contemplated. Such enhancers are contacted with the surface of the matrices via emersion, spraying, or other suitable techniques.

The tablet compositions may include these and other ingredients in the amounts shown in the following table.

| INGREDIENT | BROAD RANGE (PARTS) | NARROW RANGE (PARTS) |
|---|---|---|
| Carrier | 40–90 | 50–75 |
| Bioaffecting Agent | 1–60 | 10–40 |
| Binder | 0.01–20 | 0.1–10 |
| Others | Balance | Balance |

Matrix crystallization, or "recrystallization" (term used when the original feedstock is crystalline) may take place in the presence of the bioaffecting agent(s) and the flow control agent(s) and may be effected before or after non-matrix ingredients are added and before or after tablet formation (by, for example, compaction or compression).

U.S. Pat. No. 5,622,719 deals with comestible units made by mixing additives with shearform matrices, molding them, and crystallizing the molding units. U.S. Pat. 5,895,664, shows a process of making comestible units wherein crystallization of the shearform matrix is started before or after non-matrix ingredients are added, but before the matrix/additive combination is compacted.

Flosses, or matrices, for use in the invention may be made using processes and devices described in one or more of the following patents and patent applications, all assigned to applicants' assignee: U.S. Pat. Nos. 5,429,836; 5,587,172; 5,851,454. U.S. Pat. application Ser. No. 08/854,344, filed May 12, 1997 (#0007.US), and U.S. Pat. No. 5,834,033 and PCT publications WO 95/34290, published Dec. 21, 1995, and WO 95/34293, published Dec. 21, 1995.

All of the disclosures mentioned above are hereby incorporated by reference.

Tablet compositions can be tableted by single punch equipment or molding device, or they can be compressed using various conventional devices, such as Stokes D3 press and the Kilian T200 devices at temperatures and humidities described above.

The following example further illustrates the invention.

EXAMPLE

Acetaminophen microspheres (APAP) were melt-blended with glycerin and tableted along with a shearform matrix (floss) using the following procedure.

The APAP microspheres/glycerin were blended in a Turbula mixer for about 3 minutes.

The floss consisted of 84.75 parts sucrose, 15 parts sorbitol, and 0.25 parts TWEEN 80. The floss was made on a 5" pharmaceutical plate head at 183° C. and 60Hz. The floss was chopped for 30 seconds in a Stephan mixer on high speed.

The tablet mix contained:

| INGREDIENT | PARTS |
|---|---|
| APAP Microspheres | 47.35 |
| Floss | 47.68 |
| Glycerine | 3.00 |
| Lemon Juice | 0.25 |
| Alpine Creme | 0.25 |
| Citric Acid | 0.25 |
| Aspartame | 0.67 |
| CABOSIL | 0.50 |
| Colorant | 0.05 |

One fourth of the chopped floss was mixed with the APAP/glycerin blend and stirred in a Hobart mixer for 1 minute. Another quarter of floss was then added; this process was repeated. The flavor was pre-blended with the final one-quarter of floss, then added to the glycerin-containing mixture. The blend, in a closed container, was stored in a refrigerator at 8° C.

The mix was removed from the refrigerator and tabletted at 22.4% relative humidity and at 28.2° F. The mix was molded in a ¾-inch punch and die set on a Stokes D3 tablet press at 30 Hz and 60Hz speeds to yield 1.25 gram tablets of 1 lb. hardness. Tablets made at both speeds melted in the mouth in less than 10 seconds.

Reasonable variations, such as those which would occur to a skilled artisan, can be made herein without departing from the scope of the invention.

We claim:

1. A process for improving the flow properties of a mixture of ingredients to be tabletted comprising subjecting said mixture of ingredients to a temperature of less than about 15° C. and a controlled humidity environment for a period of time sufficient to reduce the adhesion properties and improve the flow properties of said mixture, wherein said mixture comprises a saccharide-based carrier matrix and a liquid binder.

2. The process of claim 1 wherein the composition comprises:
   (a) about 40 parts to about 90 parts saccharide-based carrier;
   (b) about 1 parts to about 60 parts bioaffecting agent; and
   (c) about 0.01 parts to about 20 parts of at least one binder.

3. The process of claim 2 wherein (c) comprises glycerin.

4. A process for producing tabletted comestibles comprising:

providing a mixture of ingredients to be tabletted comprising a saccharide-based carrier matrix and a liquid binder;

subjecting said mixture to temperatures of less than about 15° C. and a controlled humidity environment wherein the adhesion properties of the mixture are reduced and the flow properties are improved; and processing said subjected mixture into tabletted comestible units at a temperature less than about 15° C. and a controlled humidity environment to maintain the improved flow properties of the subjected mixture during said processing.

5. The process of claim 4 wherein the tableting composition comprises:
   (a) about 40 parts to about 90 parts saccharide-based carrier;
   (b) about 1 parts to about 60 parts bioaffecting agent; and
   (c) about 0.01 parts to about 20 parts of at least one binder.

6. The process of claim 4 wherein the temperature is from about −20° C. to about 15° C. and the relative humidity is less than about 40%.

* * * * *